United States Patent [19]
Jednákovits et al.

[11] Patent Number: 6,143,741
[45] Date of Patent: Nov. 7, 2000

[54] PHARMACEUTICAL PRODUCTS FOR CURING AND PREVENTING ILLNESSES CONNECTED WITH THE MALFUNCTION OF VASCULAR ENDOTHELIAL CELLS

[75] Inventors: Andrea Jednákovits, Szentendre; László Ürögdi, Budapest; Ede Márványos, Budapest; Mihály Barabás, Budapest; István Kurucz, Budapest; Ernö Bácsy, Budapest; László Korányi, Budapest; Sándor Erdö, Budapest; György Dormán, Budapest; Márta Vitai, Sümeg; György Schmidt, Budapest; Márta Sinka, Budapest; Magdolna Török, Mátészalka, all of Hungary

[73] Assignee: BIOREX Kutato es Fejleszö Rt., Veszprém, Hungary

[21] Appl. No.: 09/230,941
[22] PCT Filed: Aug. 6, 1997
[86] PCT No.: PCT/HU97/00044
  § 371 Date: Dec. 6, 1999
  § 102(e) Date: Dec. 6, 1999
[87] PCT Pub. No.: WO98/06400
  PCT Pub. Date: Feb. 19, 1998

[30] Foreign Application Priority Data

Aug. 9, 1996 [HU] Hungary ................................. 96 02204
Aug. 4, 1997 [HU] Hungary ................................. 97 01349

[51] Int. Cl.$^7$ .................................................. A61K 31/535
[52] U.S. Cl. ............................................................. 514/229.2
[58] Field of Search ........................................... 514/229.2

[56] References Cited

U.S. PATENT DOCUMENTS 4,187,220  2/1980  Takacs et al. .

FOREIGN PATENT DOCUMENTS

WO 90/04584  5/1990  WIPO .
WO 92/03130  3/1992  WIPO .
WO 95/30649  11/1995  WIPO .
WO 97/00251  1/1997  WIPO .
WO 97/16439  5/1997  WIPO .

Primary Examiner—Raymond Henley, III
Attorney, Agent, or Firm—Finnegan, Henderson, Farabow, Garrett & Dunner, L.L.P.

[57] ABSTRACT

The invention relates to a method of treating or preventing illnesses resulting from damaged endothelial cells, wherein the method comprises administering to a patient a product comprising hydroxylamine derivatives of the general formulae (I)

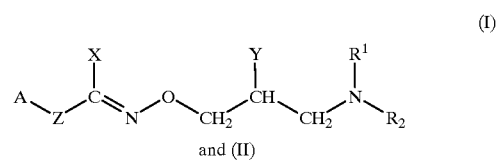

and (II)

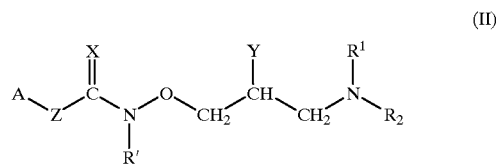

with the proviso that in the compounds of general formula (I) when X comprises a —NR$^3$R$^4$ group and Y comprises a hydroxyl group, the X group is condensed with the Y substituent to form an intramolecular ring represented by general formula (III)

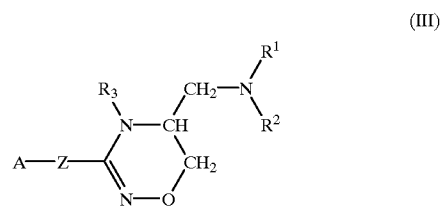

15 Claims, 4 Drawing Sheets

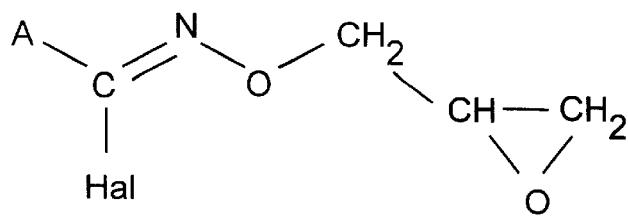 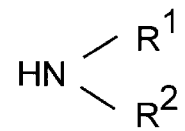
FIG. 8  FIG. 9
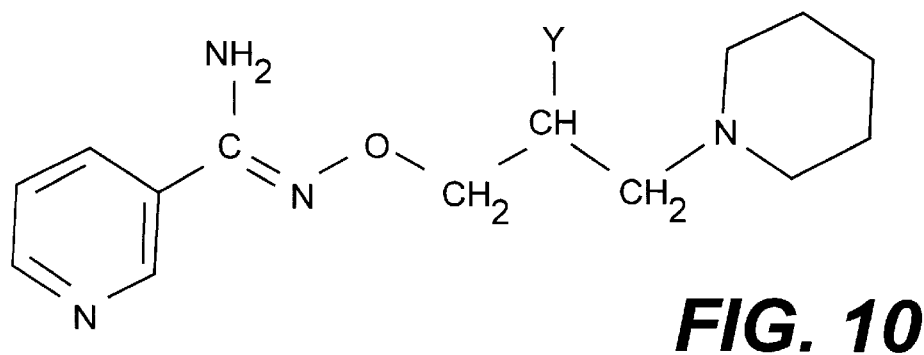
FIG. 10
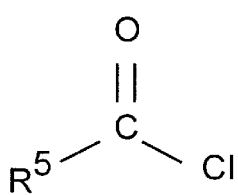 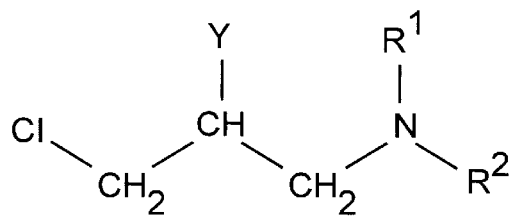
FIG. 11  FIG. 12

PHARMACEUTICAL PRODUCTS FOR CURING AND PREVENTING ILLNESSES CONNECTED WITH THE MALFUNCTION OF VASCULAR ENDOTHELIAL CELLS

This is a 371 of PCT/HU97/00044 filed Aug. 6, 1997.

TECHNICAL FIELD OF THE INVENTION

The invention concerns products for curing or preventing diseases resulting from the damaging of the vascular endothelial cells, which contain a hydroxylamine-derivative of general formula (I) or (II) as the effective agent.

BACKGROUND OF THE INVENTION

The normal functioning of the vascular endothelial cells is of crucial importance for the body. These cells form an edge surface between the circulating blood and the elements of the vein wall performing thrombogenous activity. The role of the vascular endothelial cells in homeostasis is quite varied:

they participate in the two-way transport of substances originating from the blood and the tissues, they form a barrier for the macromolecules, these cells are the location of the synthesis and the decomposition of the mediators acting in the regulation of the interaction between the cellular elements of the vein wall and the blood (e.g. fibrinogen, collagen, proteoglycanes, $PGI_2$, EDRF (NO), EDHF, endothelin-1, angiotensin-II), they initiate the migrational, proliferative, and thrombolytic processes contributing to histic reparation, they sustain the thromboresistance of the vein wall [Rubányi, G., J. Cardiovasc. Pharmacol. 1993, 22 (42. Suppl., p S1–14]

The impairment of the endothelium results in atherosclerosis. The impairment leading to the deterioration of the endothelium can occur at mechanic intervention, for example catheterisation, and also as the result of biochemical and immunological processes.

As the first step of the formation of atherosclerotic plaque, cells filled with lipids accumulate in the intima of the arteries (Steinberg D. et al., JAMA 264–304, 1990). These cells— especially monocytes and macrophages originating from the blood—first stick to the endothelium, and then penetrate the intima. The injury of the endothelial cells may also contribute to the adhesion, although no morphological alteration is visible in the early phase. The oxidation of the LDL particles may result in their incorporation by the monocytes located in the intima, and the monocytes thus become foam cells. These foam cells form the lipid-streaks, the earliest form of arteriosclerotic alteration.

In the later stages, bleeding, necrosis, neovascularisation, and sclerosis occur, and in the course of these, the intergrown plaque forms, which then taper the arteries (Ip. JH, Fuster et al., J. Am. Coll. Cardiol 15:1667, 1990).

Thrombosis may occur at various stages of atherosclerosis. Repeated thrombosis leads to vascular obstruction and thromboembolic illnesses, such as coronary thrombosis, the thrombosis of the brain vessels, or peripheral vascular illnesses.

In a clinical sense, "endothelial dysfunction syndrome" refers to generalised or localised vessel spasm, thrombosis, arteriosclerosis, and restenosis. Attempts to cure these illnesses have included interventional clinical techniques, bypass surgery, and medicinal treatment.

Only a few existing drugs may be suitable for the "treatment" of endothelial dysfunction. They fall into four major categories:

substitution for natural "protective" endothelial substances (e.g. stable analogues of $PGI_2$, nitrovasodilators, rt-PA /recombinant tissue plasminogen activator/)

inhibitors or antagonists of endothelium-derived contracting factors (e.g. ACE inhibitors, angiotensin II receptor antagonists; $TXA_2$-receptor antagonists)

cytoprotective agents (e.g. the free-radical scavengers superoxide dismutase and probucol, and free radical production inhibitor lazaroids)

lipid-lowering drugs.

Although none of them were originally designed for this target, their already proven clinically beneficial effects in the case of certain illnesses may involve the protection or restoration of normal endothelial function. The rationale behind innovative therapies in this category is the restoration of normal endothelial cell lining, where these cells themselves will "do the job". Potential approaches may include stimulation of regrowth of normal endothelium, or by new emerging therapeutic modalities based on recombinant DNA technology (Science 1990; 249: 1285–8). According to the data available, no recognised drug fulfils these criteria.

These days no medicine or medicine-candidate is known to act directly on the endothelium, and thus none is suitable for treating endothelial dysfunction. Therefore, there is great therapeutical demand for a medicine which is capable of preventing, reversing, or at least slowing dowin the formation of complication symptoms, or decreasing the occurrence of the illness.

SUMMARY OF THE INVENTION

In the course of our research we have found that the hydroxylamine-derivatives of general formula (I) and (II) perform a strong protecting and regenerative effect on vascular endothelial cells, and are capable of preventing. their impairment of various origins.

In the general formulae (I) and (II), $R^1$ and $R^2$ independently refer to a hydrogen atom or a straight or branched alkyl group of 1 to 6 carbon atoms, or $R^1$ and $R^2$ together with the nitrogen atom in-between form a saturated 5–7 membered heterocyclic group, containing optionally further nitrogen and/or oxygen heteroatoms, A refers to a straight or branched alkyl group of 4 to 12 carbon atoms, a phenyl group, substituted or unsubstituted, containing preferably an alkyl-, haloalkyl- or nitro group as substituent, or a 5–6 membered heteroaromatic ring containing nitrogen, oxygen or sulphur, in the compounds of general formula (I), Z refers to a covalent bond, and in the compounds of general formula (II) to a covalent bond or a =NH group, in the compounds of general formula (I), X refers to a halogen atom or to a —$NR^3R^4$ group, wherein $R^3$ and $R^4$ independently refer to a hydrogen atom or a straight or branched alkyl group of 1 to 6 carbon atoms, while in the compounds of general formula (II) X refers to an oxygen atom, in the compounds of general formula (II), R' refers to a hydrogen atom or a straight or branched alkyl group of 1 to 6 carbon atoms, and in general formulae (I) and (II), Y refers to a hydrogen atom, a hydroxyl group or an acyloxy group, which contains preferably the acyl part of a long chain fatty acid of 8 to 22 carbon atoms, or of a cyclic aromatic carboxylic acid as its acyl component, and in the compounds of general formula (I) wherein X refers to a —NR³R⁴ group and Y refers to a hydroxyl group, the X group is condensed with the Y substituent and forms an intramolecular ring.

The salts and the optically active forms of these compounds are also effective compounds.

Those compounds of general formula (I) that have X referring to a —NH₂ group, and A referring to an unsubstituted phenyl- or pyridyl-group, and in which Y refers to a hydroxyl group are already known from the published French patent application of No. 2362 845 A1. These compounds are, according to the above quoted patent application, selective beta-blockers, and are thus suitable for the treatment of diabetic angiopathy.

Those compounds of general formula (I) that have X referring, to a halogen atom, Y referring to a hydroxyl group, and A to an unsubstituted or substituted phenyl- or pyridyl-group are already known from the published PCT patent application of No. WO 90/04584 A1. These compounds have a selective beta-blocking effect, and are thus suitable as effective agents in the treatment of diabetic angiopathy.

Those compounds of general formula (II) that have A referring to a phenyl- (unsubstituted or substituted by a haloalkyl-group), pyridyl-, or thienyl-group, Z referring to a covalent bond, R' referring to a hydrogen atom, and Y to a hydroxyl group are already known from the Hungarian patent application of No. 2385/92, published under No. T/66350. These compounds have an anti-ischaemic and anti-anginetic effect, and are thus well usable in the therapy of vein complications connected with diabetes mellitus.

Those compounds of general formula (I) that have A referring to an aromatic or heteroaromatic ring and X to a halogen atom, while Y refers to a hydrogen atom are already known from the published PCT patent application of No. WO 95/30649 A1. These compounds are of an anti-ischaemic effect, and can be best used in the treatment of the occurrences of ischaemia of which hypertonic veins and thrombocyte aggregation are characteristic.

In none of the above quoted specifications is it written that the described compounds should have any effect on the vascular endothelial cells.

As we have mentioned above, our research has proved the compounds of general formulae (I) and (II) to be effective on the endothelial cells of the cardiovascular and the cerebrovascular systems. In the experiments to be dealt with in detail later, it has been observed that these compounds are capable of blocking or restoring the damaging of these cells. Thus, these compounds may be used as effective substance in therapeutical products which are used in the treatment of illnesses resulting from the abnormal functioning or the damaging of the endothelial cells, especially cardiovascular and cerebrovascular illnesses, hypertension, hyperhomocysteinaemia, and peripheral vascular diseases.

Based on this observation, the invention consists of the application of the hydroxylanmine derivatives of general formulae (I) and (II)—wherein R¹ and R² independently refer to a hydrogen atom or a straight or branched alkyl group of 1 to 6 carbon atoms, or R¹ and R² together with the nitrogen atom in-between form a saturated 5–7 membered heterocyclic group, containing optionally further nitrogen and/or oxygen heteroatoms, A refers to a straight or branched alkyl group of 4 to 12 carbon atoms, a phenyl group, substituted or unsubstituted, containing preferably an alkyl-, haloalkyl- or nitro group as substituent, or a 5–6 membered heteroaromatic ring containing nitrogen, oxygen or sulphur, in general formula (I), Z refers to a covalent bond, and in general formula (II) to a covalent bond or a =NH group, in general formula (I), X refers to a halogen atom or to a —NR³R⁴ group, wherein R³ and R⁴ independently refer to a hydrogen atom or a straight or branched alkyl group of 1 to 6 carbon atoms, while in general formula (II) X refers to an oxygen atom, in general formula (II), R' refers to a hydrogen atom or a straight or branched alkyl group of 1 to 6 carbon atoms, and in general formulae (I) and (II), Y refers to a hydrogen atom, a hydroxyl group or an acyloxy group, which contains preferably the acyl part of a long chain fatty acid of 8 to 22 carbon atoms, or of a cyclic aromatic carboxylic acid as its acyl component, however, in certain types of compounds of general formula (I) wherein X refers to a —NR³R⁴ group and Y refers to a hydroxyl group, the X group is condensed with the Y substituent and forms the intramolecular ring represented by general formula (III), in which formula A, Z, R¹ and R² have the same reference as above, furthermore, of the salts and optically active forms of these compounds for the production of medicine used for the treatment or prevention of illnesses connected with the dysfunction of the endothelial cells.

The invention also relates to pharmaceutical products used for the treatment and prevention of illnesses in connection with abnormal functioning of the vascular cells which contain, as effective substance (apart from the usual carrier substances and auxiliary substances used in pharmaceutical compositions) a compound of general formula (I) or (II) in 0.5–95.5 m/m %, or in certain cases the salts or optically active forms of these compounds, and in these formulae the references of R¹, R², A, Z, X, Y and R' are the same as above.

Those compounds of general formula (I) and (II) are preferred for the application described in the invention, wherein A refers to a pyridyl-, a thienyl-, or a phenyl-, nitrophenyl- or trifluoromethylphenyl group. Those compounds of general formula (I) are also preferred wherein X refers to a chloro atom or to a NH₂ group. Of these latter compounds particularly preferred are those which contain an intramolecular ring formed by the condensation of groups X and Y. Also preferred are those compounds of general formula (II), wherein R' refers to a hydrogen atom, and those compounds of general formula (I) or (II) wherein Y refers to a hydrogen atom or a hydroxyl group. In all these listed categories preferred are those compounds wherein the NR¹R² group refers to a piperidino- or dialkylamino group.

The following compounds of general formula (I) and (II) are especially preferred for the invention:

N-[2-benzoyloxy-3-(1-piperidinyl)propoxy]-3-pyridinecarboximidamide (Z)-2-butenedioate (1:1) (compound No. 1.)

N-[2-palmitoyloxy-3-(1-piperidinyl)propoxy]-3-pyridinecarboximidamide monohydrochloride (compound No. 2.)

N-[3-[(1,1-dimethylethyl)amino]-2-hydroxypropoxy]-3-trifluoromethylbenzenecarboximidoyl chloride monohydrochloride (compound No. 3.)

N-[2-hydroxy-3-(1-piperidinyl)propoxy]-2-thiophenecarboximidoyl chloride monohydrochloride (compound No. 4.)

N-[2-hydroxy-3-(1-piperidinyl)propoxy]-benzenecarboximidoyl chloride monohydrochloride (compound No. 5.)

N-[2-hydroxy-3-(1-piperidinyl)propoxy]4-pyridinecarboximidoyl chloride (Z)-2-butenedioate (1:1) (compound No. 6.)

N-[2-hydroxy-3-(1-piperidinyl)propoxy]-2-nitrobenzenecarboximidoyl chloride monohydrochloride (compound No. 7.)
N-[3-(1-piperidinyl)propoxy]-3-pyridinecarboximidoyl chloride dihydrochloride (compound No. 8.)
N-[3-(1-piperidinyl)propoxy]-3-nitrobenzenecarboximidoyl chloride Monohydrochloride (compound No. 9.)
N-[3-[(1,1-dimethylethyl)amino]-2-hydroxypropoxy]-3-trifluoromethylbenzamide (compound No. 10.)
N-hexyl-N'-[2-hydroxy-3-(1 -piperidinyl)propoxy]-urea (compound No. 11.)
N-hexyl-N'-[3-(1-piperidinyl)propoxy]-urea (compound No. 12.)
5,6-dihydro-5-(1-piperidinyl)meithyl-3-(3-pyridyl)-4H-1,2,4-oxadiazine (compound No. 13.)

BRIEF DESCRIPTION OF THE DRAWINGS

FIG. 8 represents an epoxy compound of general formula (VIII).

FIG. 9 represents an amine of general formula (IX).

FIG. 10 represents a compound of general formula (X).

FIG. 11 represents an acid chloride of general formula (XI).

FIG. 12 represents a halogen-based compound of general formula (XII).

Figure 1:
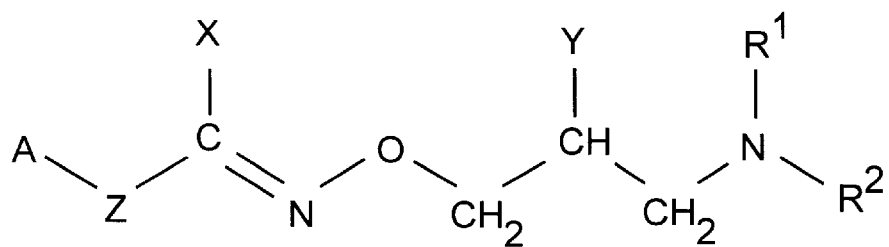
FIG. 1 represents a hydroxylamine derivative of general formula (I).
Figure 2:
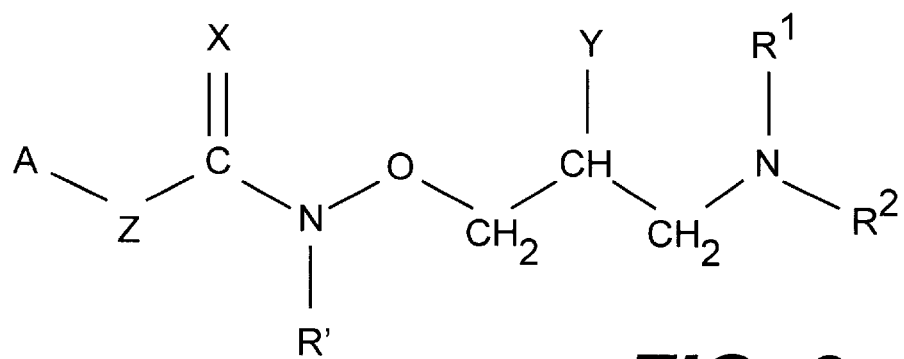
FIG. 2 represents a hydroxylamine derivative of general formula (II).
Figure 3:
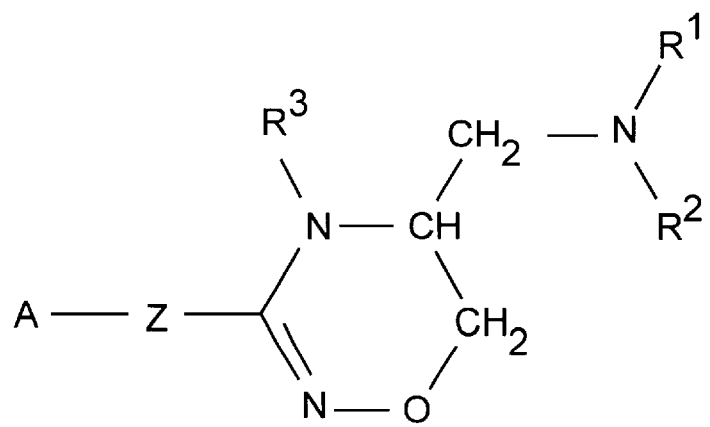
FIG. 3 represents a compound of general formula (III) which is a compound of general formula (I) wherein a nitrogen containing X group is condensed with the Y substituent to form an intramolecular ring.
Figure 4:
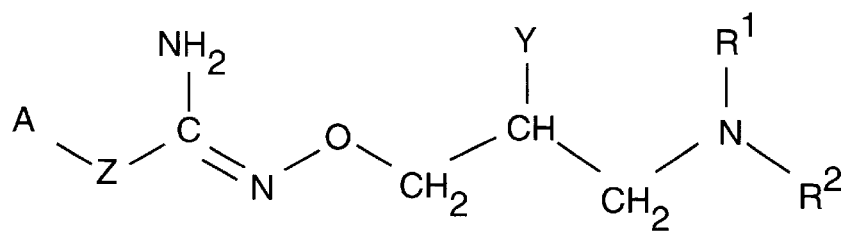
FIG. 4 represents an intermediate compound of general formula (IV), wherein X is —NH$_2$.
Figure 5:
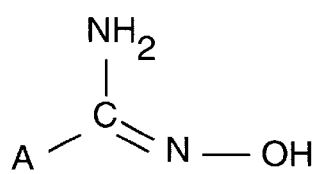
FIG. 5 represents an amidoxim of general formula (V).
Figure 6:
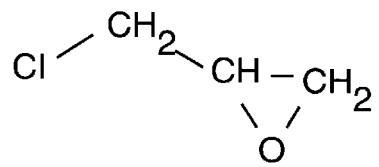
FIG. 6 represents an epichlorohydrin of general formula (VI).
Figure 7:
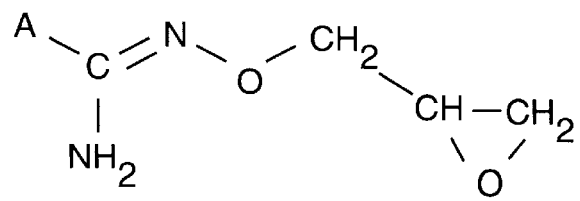
FIG. 7 represents an intermediate compound of general formula (VII).
Figure 13:
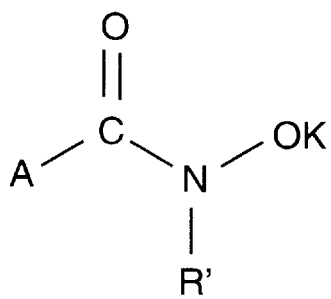
FIG. 13 represents an alkali-hydroxamate of general formula (XIII).
Figure 14:
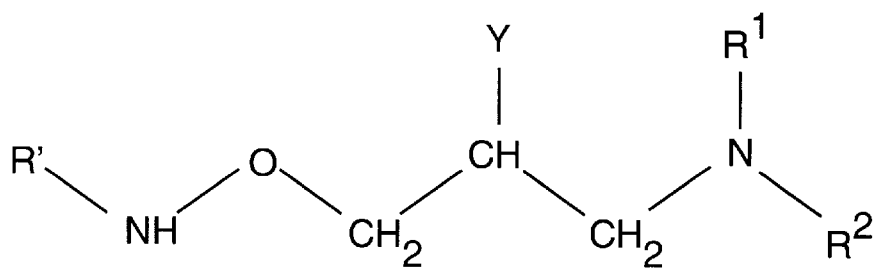
FIG. 14 represents an amino compound of general formula (XIV).
Figure 15:
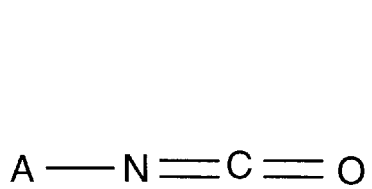
FIG. 15 represents an isocyanate-based compound of general formula (XV).
Figure 16:
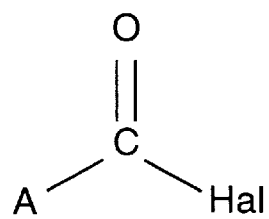
FIG. 16 represents a compound of general formula (XVI).

Those compound of general formula (I) in which X refers to halogen atom may be prepared by reacting an amidoxim of general formula (V), wherein A has the same reference as above with an amino-chloro-propane derivative, wherein $R^1$, $R^2$ and Y have the same references as above and the —NH$_2$ group of the resulting intermediate of general formula (IV), wherein Z refers to covalent bond while the other substituents have the same references as above is replaced with a halogen atom by diazotation. In cases when a compound of general formula (I) containing a hydroxyl group as Y substituent is produced the necessary amino-chloro-propane derivative of general formula (XII) containing a hydroxyl group as Y substituent may be produced from epichlorohydrin of formula (VI) and an amine of general formula (IX), wherein $R^1$ and $R^2$ have the same references as above. An alternative procedure is to react the epichlorohydrine with the amidoxim of general formula (V) first, and then to diazotate the resulting intermediate of general formula (VII), wherein A refers to the same as above and to react the epoxy-compound of general formula (VIII), wherein A refers to the same as above with the amine of general formula (IX).

Those compounds of general formula (I), wherein Y refers to an acyloxy group may be produced by a reaction of the suitable compounds of general formula (I) containing a hydroxyl group in the place of Y, and acid chlorides of general formula (XI), wherein $R^5$ refers to a long chain alkyl or to an aryl group.

The compounds of general formula (II) containing covalent bonds in the place of Z may be produced by one of the following methods:

(i) connecting an alkali-hydroxamate of general formula (XIII) wherein A and R' have the same reference as above and K refers to the cation of an alkaline metal, and a halogen compound of general formula (XII) wherein $R^1$, $R^2$ and Y have the same references as above, or (ii) the reaction of an amino compound of general formula (XIV) wherein $R^1$, $R^2$, Y and R' have the same reference as above, and an acid halogenide wherein A has the same reference as above, while those compounds of general formula (II) which contain a covalent bond in the place of Z, and a hydrogen atom in the place of R' may also be produced—beyond methods (i) and (ii)—by the following methods:

(iii) the diazotation in a halogen-free environment of a suitable compound of general formula (I) containing a —NH$_2$ group in the place of X, and a covalent bond in the place of Z, or (iv) the hydrolysis of a suitable compound of general formula (I) containing a halogen atom in the place of X.

Those compounds of general formula (II) wherein A refers to an alkyl group and Z refers to a =NH group may be produced by the reaction of a compound of general formula (II) wherein $R^1$, $R^2$, Y and R' have the same references as above, in an organic solvent, preferably in chloroform, with an equimolar amount if alkylisocyanate wherein A refers to an alkyl group.

The compounds of general formula (III) are special cases of the compounds of general formula (I) wherein a nitrogen containing X group is condensed with the Y substituent to form an intramolecular ring.

Such compounds may be produced by the reaction of a compound of general formula (I) (wherein Y refers to a hydroxyl group) with an excess of thionyl chloride, followed by the ring closure of the resulting intermediate compound of general formula (IV) (wherein Y refers to a chlorine atom, while the other substituents have the same references as above) with an excess of potassium-terc-butoxide boiled in an organic solvent (preferably in t-butanol).

The hydroxylamine derivatives of the invention bear surprising pharmacological properties. It is to be noted especially, that they do not only regenerate the endothelial cells morphologically, but also fimctionally, that is, due to their effect the endothelial cells of the good tolerability of these compounds is also remarkable. These characteristics form the grounds for the pharmaceutical use of the hydroxylamine derivatives of general formulae (I) and (II). These medicines may be used to treat cardio- and cerebrovascular diseases of humans and animals, such as hypertension, hyperhomocysteinaemia and peripheral vascular diseases.

Among cardiovascular diseases, these compounds may be best used in the cases of coronary artery diseases, atheroschlerosis, restenosis following balloon angioplasty, and coronary bypass surgery, and among cerebrovascular diseases in the cases of cerebral artery occlusion, the hydroxylamine derivatives of general formulae (I) and (II) may also be applied, in the treatment of hypertension against cases resulting from essential, renal, pulmonal and endocrine diseases, while in the therapy of peripheral vascular diseases they are best used when aortic stenosis occurs in the legs.

The compounds of the invention may also be used to counteract susceptibility for illness due to the genetically determined or temporary weakening of the protective mechanism. The usual dose depends on the patient treated and the illness in hand and may vary in the range of 0.1–200 mg/kg, preferably of 1–50 mg/kg, daily. This may mean, for example, that a daily dose for human therapy is between 10 to 200 mg orally, 1 to 15 mg rectally, or 2 to 20 mg parenterally, for adult patients.

Suitable pharmaceutical compositions may be for example solid substances or liquids, in any kind of drug formulations generally used in human or veterinary therapy, such as simple or coated tablet, gel capsule, granulates, solution, syrup, suppository, lyophilised or not lyophilised injectable product; these may be produced by the usual methods. The effective substance may be carried by the vehicles usual for these types of pharmaceutical products, such as talc, gum Arabic, lactose, starch, magnesium stearate, cocoa-butter, aqueous or non-aqueous carriers, animal or plant greases, paraffin derivatives, glycols, various moistening, dispersing, or emulgating substances and preservatives.

The biological effects of the compounds of the invention represented by the general formulae (I) and (II) are illustrated through the following results of the vasorelaxing effect test performed in vitro on rats, and of the thoracic aorta morphological test. Three-month-old, spontaneously hypertensive (SH) rats were treated for 1 month with the various tested compounds.

THE VASORELAXING EFFECT OF THE TESTED HYDROXYLAMINE DERIVATIVES ON THE THORACIC AORTA OF THE SH RATS (IN VITRO TEST)

The test was performed according to the method known from the applying literature [Japan J. Pharmacol., 59, 339–347 (1992)]. The SH rats were narcotised with Nembutal (40 mg/kg, i.p.), and their thoracic aorta was then taken out and placed in an oxygenated (95% $O_2$+5% $CO_2$) Krebs-Henseleit solution. The composition of the solution (mM): NaCl 118, KCl 4, 7, $CaCl_2$ 2, 52, $MgSO_4$ 1, 64, $NaHCO_3$ 24, 88, $KH_2PO_4$ 1, 18, glucose 5, 5. The 3 mm long aortic rings were suspended in a 20 ml organ bath of 37° C. The resting tension was 1 g, which was sustained throughout the experiment. During the 1 hour equilibration period the medium of the organ bath was changed every 20 minutes. The vessels were contracted with $10^{-6}$M methoxamine (approx. 80% of max. contraction). After reaching the maximum contraction, the vasodilation induced by acetylcholine (Ach) ($10^{-6}$–$10^{-4}$M) and functional integrity of the endothelium was tested. The contraction force was measured with an isometric strain gauge probe (SG-01D, Experimetria Ltd), and registered on an OH-850 polygraph (Radelkis). The results of the tests are summarised in table No. 1.

TABLE 1

The vasorelaxing effect of the compounds of the invention on the thoracic aorta of SH rats (in vitro test)

| Substances/Doses | Ach doses (M) | | |
|---|---|---|---|
| | $10^{-6}$ | $10^{-5}$ | $10^{-4}$ |
| SH control, n = 10 | 53.8 | 55.6 | 71.0 |
| Compound no. 13., n = 12; 20 mg/kg | 79.6 | 86.0 | 95.9 |
| Compound no. 5., n = 11; 5 mg/kg | 82.3 | 84.5 | 87.2 |
| Compound no. 4., n = 11; 20 mg/kg | 75.6 | 79.8 | 80.5 |
| Compound no. 6., n = 10; 5 mg/kg | 87.5 | 87.9 | 84.4 |
| Compound no. 10., n = 12; 10 mg/kg | 64.8 | 63.7 | 78.0 |
| Compound no. 1., n = 12; 20 mg/kg | 74.7 | 58.7 | 82.7 |
| Compound no. 2., n = 10 | 80.4 | 75.6 | 88.0 |
| Compound no. 11., n = 12; 20 mg/kg | 88.1 | 91.3 | 91.9 |
| Compound no. 8., n = 10; 5 mg/kg | 74.1 | 75.3 | 80.9 |
| Compound no. 3., n = 8; 10 mg/kg | 76.4 | 77.2 | 84.8 |
| Compound no. 12., n = 12; 10 mg/kg | 66.3 | 67.2 | 84.1 |
| Compound no. 7., n = 11; 5 mg/kg | 81.7 | 86.0 | 95.9 |
| Captopril, n = 8; 20 mg/kg | 88.7 | 88.2 | 94.2 |

As it is apparent from the table, in the cases of untreated hypertonic control animals the relaxation, provoked by the administration of $10^{-4}$M acetylcholine decreased to 71%, which is due to the endothelium damage caused by hypertension. The tested compounds improved this decreasing vasodilation significantly, which shows the improvement of the endothelial function.

THE MORPHOLOGICAL EXAMINATION OF THE THORACIC AORTA WITH ELECTRONMICROSCOPE

This test was performed according to the applying literature (Br. J. of Pharmacol., 1995; 115, 415–420). 1 $mm^2$ segments of the aorta-wall of the thoracic aorta of the rats were cut out, which were then fixed at room temperature with 2.5% glutaraldehyde. This was followed by a post-fixation with 1% osmium tetroxide, which lasted for one hour. Afterwards, the tissue segments were dehydrated with ethanol, and bedded into Durcupan ACM. The excisions were evaluated in a qualitative manner based on the photograph taken on a Hitachi 7100 electronmicroscope. The results of these tests are shown in table No. 2.

The results of the morphological tests were expressed on a scale of 1 to 5, depending on the extent to which the treatment with the tested compounds restored the endothelial damage caused by hypertension, that is, the extent of regenerating activity. On the scale, 1 represents cases where there was no regeneration to be observed, 2 stands for weak, 3 for medium, 4 for good, while 5 represents strong regeneration.

In comparison with the untreated control significant protective or regenerative effect was observed after treatment with the hydroxylamine derivatives of general formulae (I) and (II) of the invention. Due to the treatment, a thin protective layer formed over the injured subendothelium, which was composed of cells containing an active nucleus and rich cytoplasm. Regeneration appeared quite effective in the majority of the cases.

TABLE 2

The electromicroscopic evaluation of the effects of the compounds
of the invention on the thoracic aorta of SH rats (morphological test)

| Substances Doses | Extent of Regeneration |
|---|---|
| SH control (phys. salt) | 1 |
| Compound no. 13., 20 mg/kg p.o. | 5 |
| Compound no. 5., 5 mg/kg p.o. | 5 |
| Compound no. 4., 5 mg/kg p.o. | 5 |
| Compound no. 10., 10 mg/kg p.o. | 4 |
| Compound no. 1., 20 mg/kg p.o. | 3 |
| Compound no. 11., 20 mg/kg p.o. | 4 |
| Compound no. 8., 5 mg/kg p.o. | 3 |
| Compound no. 9., 5 mg/kg p.o. | 3 |
| Compound no. 12., 5 mg/kg p.o. | 4 |
| Compound no. 14., 20 mg/kg p.o. | 3 |
| Captopril 100 mg/kg p.o. | 3 |

These experimental data also support the assumption that the compounds of general formula (I) and (II) are able to regenerate the endothelium not only fulnctionally but morphologically as well. Upon chronic treatment these compounds resulted in more pronounced morphological regeneration than the reference substance Captopril.

EXAMINATION OF THE INFARCTED AREA ON SPONTANEOUSLY HYPERTENSIVE (SH) RATS AFTER ONE MONTH ORAL TREATMENT

Exerimental Groups

1. SH-age matched control
2. Verapamil (as a reference drug), 50 mg/kg p.o.
3. Compound No. 13., 20 mg/kg p.o.
4. Compound No. 13., 50 mg/kg p.o.
5. Compound No. 5., 5 mg/kg p.o.
6. Compound No.4., 5 mg/kg p.o.

Induction of Infarction

Myocardial ischaemia was induced by a temporary occlusion of the main left coronary artery, according to Griswold et al. (J. Pharmacol. Methods 1988. 20: 225–35). SH rats were anaesthetized with sodium pentobarbital (50 mg/kg ip.). After tracheotomy, the animals were ventilated with room air by a respirator for small rodents (model: Harvard 552), with a stroke volume of 1,5–2 ml/100 g and a rate of 55 strokes/min to maintain normal $pO_2$, $PCO_2$ and pH parameters.

The right carotid artery was catheterised and connected with a pressure transducer (P236B Stetham) for the measurement of systemic arterial blood pressure (BP) by means of a preamplifier (Hg-O2D Experimetria®). Heart rate (HR) was measured by a cardiotachometer (HR-01, Experimetria®). The electrocardiogram (ECG standard lead III.) was recorded on a devices recorder (ER-14, Micromed®) by means of subcutaneous steel needle electrodes. The chest was opened by a left thoracotomy and the heart was exteriorized by a gentle pressure on the right side of the rib cage. A 4/0 silk ligature was quickly placed under the main left coronary artery. The heart was replaced in the chest and the animal left to recover.

Rectal temperature was monitored and was maintained constant at 37° C.

The experimental protocol was initiated with a 15 min stabilisation period during which the observation of a sustained blood pressure less than 70 mmHg and/or the occurence of arrhythmias lead to exclusion.

Myocardial ischaemia was induced with coronary artery occlusion for 1 hour and reperfusion allowed for 1 hour. Sham operated animals underwent to all the previously described surgical procedures except coronary occlusion and reperfusion.

Quantification of Myocardial Infarction

At the end of experiment, the heart was quickly removed. The left ventricle was sliced into 2 mm thick sections parallel to the atrioventricular groove. The slices were incubated in a 0.1% solution of Nitroblue Tetrazolium grade III, pH 7,4 for 15 min. The non-infarcted area was colored blue due to formation of a precipitate that results from reaction of NBT with dehydrogenase enzymes. Loss of these enzymes from infarcted myocardium prevents formation of the precipitate; thus, the infarcted area within the risk region remains pale yellow. The LV sections were photographed (Practica) and infarcted area was measured by planimetry. The necrotic area was expressed as a percentage of the surface of the left ventricle.

Statistical Analysis

All values will be expressed as mean ±SEM. Comparisons between groups will be assessed by one-way ANOVA with post hoc analysis using the Student „t" test. Statistical significance will be defined as $p<0.05$.

Results

There was no significant difference in the haemodynamic parameters, left ventricular and body weights among the groups.

TABLE 3

The infarct size and the survival rate of SH rats after coronary artery occlusion and reperfusion

| Groups | Infarct size (%) | Survival rate (%) |
|---|---|---|
| Control n = 9 | 42.7 ± 1.37 | 28.13 |
| Verapamil 50 mg/kg n = 8 | 24.3 ± 2.87** | 53.3** |
| Compound No. 13. 20 mg/kg, n = 7 | 22.3 ± 3.6**,# | 77.8**,# |
| Compound No. 13. 50 mg/kg, n = 5 | 15.2 ± 3.7** | 60.0** |
| Compound No. 5. 5 mg/kg, n = 3 | 29.3 ± 2.9** | 30.0 |
| Compound No. 4. 5 mg/kg, n = 5 | 25.6 ± 4.0** | 71.4**,# |

**$p < 0.01$ vs control
$p < 0.01$ vs verapamil

Following coronary artery occlusion and reperfision, there was a marked decrease in the survival rate of the control rats. Administration of different active compounds (except compound No. 5.) and the reference substance verapamil orally for one month significantly increased the resistance of rats to myocardial ischaemia/reperflsion injury.

Compared to verapamil, the improvement was significantly higher after treatment with compound No. 13. (20 mg/kg) and compound No. 4.

The active compounds and verapamil significantly reduced the infarct size compared to the control animals. The infarct size limitation was dose-dependent. The higher dose significantly reduced the extension of the myocardial necrosis compared to verapamil.

Our experiments indicate that selected active compounds significantly reduced the extension of the myocardial necrosis and significantly improved the survival rate. Infarct size limitation occurred without any marked changes in the haemodynamic parameters, and it was significantly higher after treatment with the compounds of the invention than after administration of the reference substance verapamil.

WOUNDING MIGRATION ASSAY

HUVEC cells were isolated and cultivated according to Jaffe E. A. et al. (J. Clin. Invest., 52, 2745–2756, 1973) The assay was carried out as described by Yamamura S. et al. (J. Surg. Res., 63, 349–354, 1996). HUVEC cells were seeded on 96 well plate, previously coated with fibronectin (2 μg/well)(Sigma), and at appr. 90% confluency the monolayer was wounded along by coordinate line labeled backside of the plate. The layer injured with a Teflon cell scraper that was 1 mm in width. Well was rinsed and filled with completed RPMI 1640 medium (containing 5% of protein) for incubation (at 37° C. in 5% $CO_2$ containing air). Cells were allowed to migrate for 24 and 48 hours onto the wounded field and camera or photographs were taken through an inverted microscope (at ×60 magnification) to recording. The numbers of cells that were moved beyond the reference line counted and evaluated by image analyzer.

Treatment with the Test Compound

A serial ten step fold dilution were prepared in medium added 5 μl/well containing 95 μl of tissue culture over the wounded cell monolayer. The control culture contained no dilution of compound No. 13.

Results

After 24 hour incubation the cells spontaneously appeared in the wounded area and even an increased number was counted in the presence of test compound at a submicromolar concentration (at $10^{-7}$ and $10^{-8}$M). test compound resulted an emphatic, considerable promotion on cell migration even 48 hrs period. The wounded area was covered about 82% compared to 47% with the spontaneous migrated human endothelial cells.

TABLE 4

Results of the wounding migration test with compound No. 13.

| Doses | The covered area | | | |
|---|---|---|---|---|
| | cell/mm$^2$ | | %/mm$^2$ | |
| $10^{-8}$ (M) | 24 h | 48 h | 24 h | 48 h |
| 7 | 689 | 1009 | 56 | 82 |
| 8 | 750 | 948 | 61 | 80 |
| Non-treated* | 480 | 578 | 39 | 47 |
| Adhered cells** | 180 | | 6 | |

*Non treated control, spontaneous migration,
**Cells on the injured surface immediately after wounding start, control situation.

The repair process of damaged vascular monolayer is started with migration of endothelial cells by that way may flrther initialized reconstruction of injured area. All our data suggest that test compound may promote repair on wounded human endothelial cells with direct enhancement of migration.

The invention is illustrated in the following examples without any limitation on the scope claimed:

DETAILED DESCRIPTION OF THE PREFERRED EMBODIMENTS

Example 1

N-[2-benzoyloxy-3-(1-piperidinyl)propoxy]-3-pyridinecarboximidamide (Z)-2-butenedioate (1:1) (Compound No. 1.)

Procedure 20.9 g (75.0 mmol) of N-[2-hydroxy-3-(1-piperidinyl)propoxy]-3-pyridine-carboximidamide [Hung. Pat. 177.578 (1976)] was dissolved in 300 ml of benzene. To this solution 150 ml of 1 N sodium hydroxide solution was added, followed by dropwise addition of 19.5 ml (168 mmol) of benzoylchloride. After stirring the mixture intensively for 2 hours, 7.1 g (67 mmol) of sodium carbonate and a further portion of benzoylchloride (9.75 ml; 84 mmol) was added, and the stirring was continued overnight. The phases were then separated, the organic layer was extracted with 1N sodium hydroxide solution and water, dried and evaporated to dryness. The residue (41 g oil) was dissolved in 150 ml of acetone, and 8.7 g (75 mmol) maleic acid was added. The obtained precipitate was filtered off, washed with acetone, and dried.

Yield: 29.0 g (78%), Mp.: 194–195° C.

Example 2

N-[2-palmitoyloxy-3-(1-piperidinyl)propoxy]-3-pyridinecarboximidamide Monohydrochloride (Compound No. 2.)

Procedure 14.7 g (52.8 mmol) of N-[2-hydroxy-3-(1-piperidinyl)propoxy]-3-pyridine-carboximidamide [Hung. Pat. 177.578 (1976)] was dissolved in 160 ml of chloroform. 7.7 ml (55 mmol) of triethylamnine was added, followed by dropwise addition of a solution of palmitoylchloride (14.7 g; 56.5 mmol) in 85 ml of chloroform. The mixture was stirred overnight at room temperature. Next day further amount of 3.8 ml of triethylamine and 7.4 g of palmitoylchloride was added, and the stig was continued for one more day. The solution was extracted then with water, 5% acetic acid and water, successively, dried over anh. sodium sulphate, and evaporated to dryness.

The residue (28.2 g oil) was dissolved in ethyl-acetate, and the product was precipitated by addition of 30 ml of 1N HCl/ethyl acetate. The thick, white precipitate was filtered off, washed with ethyl acetate and dried.

Yield: 10.9 g (37%), Mp.: 110–113° C.

Example 3

N-[3-[(1,1-dimethylethyl)amino]-2-hydroxypropoxy]-3-trifluoromethylbenzenecarboximidoyl Chloride Monohydrochloride (Compound No. 3.)

Procedure

Step a)

50 g (0.245 mol) of m-trifluoromethyl-benzamidoxime and 33.7 g (0.6 mol) of potassium hydroxide was dissolved in a mixture of dimethyl sulphoxide and 170 ml of water, and the mixture was cooled to 0° C. 48 ml (0.6 mol) of epichlorohydrin was added, and the reaction mixture was stirred at 0° C. for 5 hours, then kept in a refrigerator overnight. Next day 250 ml of water was added, and the mixture was extracted with ethyl acetate (4×250 ml). The combined organic phases were washed with water, dried, treated with charcoal and evaporated to dryness, to yield m-trifluoromethyl--N-(2,3--poxypropoxy)-benzanidine, as a colourless oil.

Yield: 61 g (96%)

Step b)

To the obtained oil 400 ml of 18% of hydrochloric acid solution and 60 ml of ether were added, and the mixture was cooled to −5° C., while stirring. 17.4 g (0.25 mol) of sodium nitrite, dissolved in 60 ml of water was added slowly in 40 min., and the reaction mixture was stirred for another 20 minutes. The mixture was extracted then with ether (2×160 ml), and the combined organic phases were washed with water twice. To the ethereal solution 340 ml of 20% of sodium hydroxide solution was added, and the two-phase system was refluxed for 1 hour, while stirring. The phases were then separated, the organic layer was washed with brine until neutral, dried and evaporated to dryness to give m-trifluoromethyl-N-(2,3-epoxypropoxy)-benzimidoyl chloride, as a colourless oil.

Yield: 30.5 g (45%)

Step c)

A mixture of 1.19 g (4.2 mmol) N-[(2,3-epoxy)propoxy]-3-trifluoromethylbenzenecarboximidoyl chloride and 0.89 ml (8.5 mrnol) of tert-butylamine in 12 ml of isopropyl alcohol was refluxed for 2 hours. Solvent was removed under reduced pressure. The residue was dissolved in ethyl acetate, and 0.98 ml of methanolic hydrogen chloride solution (4.3N) was added and the mixture was concentrated to small volume under vacuum, then diluted with ether. The precipitate that formed was recovered, washed with cold ether and dried.

Yield: 0.4 8 g (32%), Mp.: 150–153° C.

IR (KBr): 3423, 3233, 2978, 2880, 2784, 1620,1570, 1479, 1441, 1400,1383, 1340, 1238, 1167, 1128, 1101, 1072, 1038, 982, 930, 897, 804, 787, 714, 694 cm$^{-1}$

Example 4

N-[2-hydroxy-3-(1-piperidinyl)propoxy]-2-thiophenecarboximidoyl Chloride Monohydrochloride (Compound No.4.)

Procedure 5.0 g (15.6 mmol) of N-[2-hydroxy-3-(1-piperidinyl)propoxy]-2-thiophenecarboximidamide monohydrochloride was dissolved in 19 ml of water, then 6.1 ml of concentrated hydrochloric acid was added. The solution was cooled to −5° C., then a cold solution of 4.4 g (63.8 mmol) of sodium nitrite in 2.4 ml of water was added dropwise. Throughout the reaction the internal temperature was maintained at 0° C. When addition was completed the mixture was stirred for a further one hour. Cold benzene (60 ml) was added and the mixture was made alkaline with slow addition of a cold solution of 3.2 g (80 mmol) of sodium hydroxide in 45 ml of water. The organic phase was separated and washed successively with 20 ml portions of water until the pH<9 (3–5 times). The organic solution was dried over anhydrous sodium sulphate, treated with charcoal, filtered and evaporated in vacuum (t<45° C.) to give 2.6 g of oil. This residue was dissolved in 5 ml of isopropyl alcohol and acidified (pH 2) with isopropyl alcohol containing dry hydrochloric acid. The product was crystallised from n-hexane to give off-white material.

Yield: 2.0 g (38%), Mp.: 115–123° C.

Following the process described in the previous example the following compounds were prepared:

Example 5

N-[2-hydroxy-3-(1-piperidinyl)propoxy]-benzenecarboximidoyl Chloride Monohydrochloride (Compound No. 5.)

Starting material: N-[2-hydroxy-3-(1-piperidinyl)propoxy]-benzenecarboximidamide Yield: 23%, Mp.: 140–145° C.

Example 6

N-[2-hydroxy-3-(1-piperidinyl)propoxy]-4-pyridinecarboximidoyl Chloride (Z)-2-butenedioate (1:1) (Compound No. 6.)

Starting material: N-[2-hydroxy-3-(1-piperidinyl)propoxy]-4-pyridinecarboximidamide In this case the final product was isolated at the end of the work-up procedure by dissolving the crude base in acetone, and adding an equivalent amount of maleic acid.

Yield: 25%, Mp.: 150–154° C.

Example 7

N-[2-hydroxy-3-(1-piperidinyl)propoxy]-2-nitrobenzenecarboximidoyl Chloride Monohydrochloride (Compound No. 7.)

Starting Material

N-[2-hydroxy-3-(1-piperidinyl)propoxy]-2-nitrobenzenecarboximidamide

Yield: 36%, Mp.: 158–162° C.

Example 8

Hiba! A könyvjelző nem létezik

N-(3-(1-piperidinyl)propoxy)-3-pyridinecarboximidoyl Chloride Dihydrochloride (Compound No. 8.)

Starting material: N-[3-(1-piperidinyl)propoxy]-3-pyridinecarboximidamide

Yield: 33%, Mp.: 178–182° C.

Example 9

N-[3-(1-piperidinyl)propoxy]-3-nitrobenzenecarboximidoyl Chloride Monohydrochloride (Compound No. 9.)

Starting material: N-[3-(1-piperidinyl)propoxy]-3-nitrobenzenecarboximidamide

Yield: 49%, Mp.: 173–175° C.

Example 10

N-[3-[(1,1-dimethylethyl)amino]-2-hydroxypropoxy]-3-trifluoromethyl-benzamide (Compound No. 10.)

Procedure 1.3 ml (15.2 mmol) of epichlorohydrin was added to a solution of 1.6 ml (15.2 mmol) of tert-butylamine in 8 ml of ethanol during 10 minutes with stirring, keeping the temperature below 20° C., and allow to stand for 3 days. Separately, 0.8 g (14.3 mmol) of potassium hydroxide was dissolved in a mixture of 20 ml of ethanol and 3 ml of water and into this solution 3.42 g (15.2 mmol) of N-hydroxy-3-(trifluoromethyl)-benzamide potassium salt and the formerly prepared solution of epichlorohydrin and tert-butylamine were added. The reaction mixture was stirred and boiled for 10 hours, then the solvent was evaporated. The residue was triturated with 20 ml of dichloromethane and 10 ml of water, the organic phase was separated, washed with 5 ml of water and 5 ml of saturated sodium chloride solution, dried over sodium sulphate, filtered and evaporated. The oily residue was crystallised in a mixture of acetone-hexane to yield white powder as title compound.

Yield: 0.85 g (17.3%), Mp.: 156–158° C.

IR (KBr): 2976, 2858, 1612, 1556, 1379, 1352, 1313, 1273, 1165, 1130, 1072, 694 cm$^{-1}$

Example 11

N-hexyl-N'-[2-hydroxy-3-(1-piperidinyl)propox]-urea (Compound No. 11.)

Procedure

To the solution of 8.0 g (45.9 nmol) of 1-aminooxy-2-hydroxy-3-(1-piperidinyl)-propane dissolved in 60 ml of chloroform 4.9 ml (45.9 mmol) of hexylisocyanate was added and the reaction mixture was stirred for 20 hours at room temperature. After addition of a further 1.6 ml (15 mmol) of hexylisocyanate, the stirring was continued for two more hours, when the solvent was evaporated in vacuum. White crystalline product was obtained by triturating with petroleum ether.

Yield: 9.9 g (72%), Mp.: 50–52° C.

IR (KBr): 3310, 2932, 2858, 2804, 1666, 1551, 1454, 1377, 1306, 1092, 1040, 995, 791, 725, 604 $cm^{-1}$

Following the process described in the previous example the following compounds were prepared:

Example 12

N-hexyl-N'-[3-(1-piperidinyl)propoxy]-urea (Compound No. 12.)

Starting material: 1-aminooxy-3-(1-piperidinyl)-propane
Yield: 85% (oil)
IR (KBr): 3354, 2932, 2856, 2810, 2777, 1666, 1543, 1486, 1377, 1308, 1155, 1134, 1076 $cm^{-1}$

Example 13

5,6-Dihydro-5-(1-piperidinyl)methyl-3-(3-pyridyl)-4H-1,2,4-oxodiazine

Procedure

Step a)

17.5 g (0.05 mole) of N-[2-hydroxy-3-(1-piperidinyl)propoxy]-3-pyridinecarbox-imidamide dihydrochloride was dissolved in 50 ml of thionyl chloride, boiled for one hour, then the mixture was evaporated to dryness. The residue was dissolved in 300 ml of methanol, treated with charcoal and after filtration the solvent was evaporated in reduced pressure. The residue was dissolved in the minimum amount of ethanol and refrigerated to yield crystalline N-[2-chloro-3-(1-piperidinyl)propoxy]-3-pyridinecarboximidamide dihydrochloride as intermediate compound.

Yield: 13.2 g (71%), Mp.: 127–145° C.

Step b)

13.2 g (35.7 mrnmole) of N-[2-chloro-3-(1-piperidinyl)propoxy]-3-pyridinecarbox-imidamide dihydrochloride was added to a solution of 16.5 g (143.5 mmole) of potassium tert-butoxide dissolved in 150 ml of tert-butanol. The mixture was boiled for 6 hours, then evaporated in vacuum. 100 ml of 5% sodium hydroxide solution was added and the mixture was extracted three times with 300 ml portions of ethyl acetate. The organic layer was dried over sodium sulphate, filtered and evaporated to dryness. The residue was triturated with diethyl ether to yield the title compound as white crystals.

Yield: 3.5 g (38%), Mp.: 157.5–158° C.

Example 14

Tablets

For the production of 200 mg tablets containing 50 mg of effective substance use:

50 mg of N-[2-hydroxy-3-(1-piperidinyl)propoxy]-benzenecarboximidoyl chloride monohydrochloride 129 mg of microcrystalline cellulose (e.g. "Avicel ph 102")

20 mg of polyvinyl-pirrolidone (e.g. "Polyplasdone XL")

1 mg of magnesium stearate

Example 15

Capsules

For a 300 mg capsule use:

50 mg of N-[2-hydroxy-3-(1-piperidinyl)propoxy]-2-nitro-benzenecarboximidoyl chloride monohydrochloride 10 mg of yellow bee wax 10 mg of soybean oil 130 mg of vegetable oil 100 mg of capsule cell

Example 16

Solution

For 100 ml solution use:

500 mg of N-[2-hydroxy-3-(1-piperidinyl)propoxy]-2-thiophenecarboximidoyl chloride monohydrochloride 10 g of sorbit 0.05 g of saccharine sodium ad 100 ml of twice distilled water.

Example 17

Injection Vial

For each 2 ml injection vial containing 2 mg of effective substance use:

2 mg of 5,6-Dihydro-5-(1-piperidinyl)methyl-3-(3-pyridyl)-4H-1,2,4-oxadiazine ad 2.0 ml of physiological saline solution, pyrogen-free, sterile.

Example 18

Infusion Solution

For 500 ml of infusion solution use:

20 mg of N-hexyl-N'-[3-(1-piperidinyl)propoxy]-urea ad 500 ml of physiological saline solution, pyrogen-free, sterile.

What is claimed is:

1. A method of treating or preventing. illnesses resulting from damaged endothelial cells said method comprising:

administering to a patient hydroxylamine derivatives of the general formulae

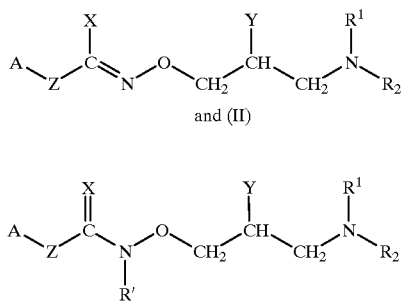

wherein $R^1$ and $R^2$ independently comprise a hydrogen atom or a straight or branched alkyl group of 1 to 6 carbon atoms, or $R^1$ and $R^2$ together with the nitrogen atom in-between form a saturated 5–7 membered heterocyclic group, optionally containing additional nitrogen and/or oxygen heteroatoms, A comprises a straight or branched alkyl group of 4 to 12 carbon atoms, a phenyl group, substituted or unsubstituted, optionally containing an alkyl-, haloalkyl- or nitro group as substituent, or a 5–6 membered heteroaromatic ring containing nitrogen, oxygen or sulphur, in general formula (I) Z comprises a covalent bond, and in general formula (II) Z comprises a covalent bond or a =NH group, in general formula (I) X comprises a halogen atom or to a —$NR^3R^4$ group, wherein $R^3$ and $R^4$ independently comprise a hydrogen atom or a straight or branched alkyl group of 1 to 6 carbon atoms, while in general formula (II) X comprises an oxygen atom, in general formula (II) R' comprises a hydrogen atom or a straight or branched alkyl group of 1 to 6 carbon atoms, and in general formulae (I) and (II) Y comprises a hydrogen atom, a hydroxyl group or an acyloxy group, which optionally contains the acyl part of a long chain fatty acid of 8 to 22 carbon atoms, or of a cyclic aromatic carboxylic acid as its acyl component, and in the compounds of general formula (I) when X comprises a —$NR^3R^4$ group and Y comprises a hydroxyl group, the X group is condensed with the Y substituent to form the intramolecular ring represented by general formula (III),

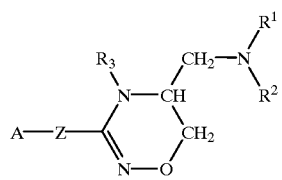

in which formula A, Z, $R^1$ and $R^2$ comprise the elements defined above or the salts and optically active forms thereof.

2. The method according to claim 1, wherein said method comprises using N-[2-benzoyloxy-3-(1-piperidinyl) propoxy]-3-pyridinecarboximidamide (Z)-2-butenedioate (1:1) as an active ingredient.

3. The method according to claim 1, wherein said method comprises using N-[2-palmitoyloxy-3-(1-piperidinyl) propoxy]-3-pyridinecarboximidamide monohydrochloride as an active ingredient.

4. The method according to claim 1, wherein said method comprises using N-[3-[(1,1-dimethylethyl)amino]-2-hydroxypropoxy]-3-trifluoromethylbenzenecarboximidoyl chloride monohydrochloride as an active ingredient.

5. The method according to claim 1, wherein said method comprises using N-[2-hydroxy-3-(1-piperidinyl)propoxy]-2-thiophenecarboximidoyl chloride monohydrochloride as an active ingredient.

6. The method according to claim 1, wherein said method comprises using N-[2-hydroxy-3-(1-piperidinyl)propoxy]-benzenecarboximidoyl chloride monohydrochloricle as an active ingredient.

7. The method according to claim 1, wherein said method comprises using N-[2-hydroxy-3-(1-piperidinyl)propoxy]-4-pyridinecarboximidoyl chloride (Z)-2-butenedioate as an active ingredient.

8. The method according to claim 1, wherein said method comprises using N-[2-hydroxy-3-(1-piperidinyl)propoxy]-2-nitrobenzenecarboximidoyl chloride monohydrochloride as an active ingredient.

9. The method according to claim 1, wherein said method comprises using N-[3-(1-piperidinyl)propoxy]-3-pyridinecarboximidoyl chloride dihydrochloride as an active ingredient.

10. The method according to claim 1, wherein said method comprises using N-[3-(1-piperidinyl)propoxy]-3-nitrobenzenecarboximidoyl chloride monohydrochloride as an active ingredient.

11. The method according to claim 1, wherein said method comprises using N-[3-[(1,1-dimethylethyl)amino]-2-hydroxypropoxy]-3-trifluoromethyl-benzamide as an active ingredient.

12. The method according to claim 1, wherein said method comprises using N-hexyl-N'-[2-hydroxy-3-(1-piperidinyl)propoxy]-urea as an active ingredient.

13. The method according to claim 1, wherein said method comprises using N-hexyl-N'-[3-(1-piperidinyl) propoxy]-urea as an active ingredient.

14. The method according to claim 1, wherein said method comprises using 5, 6-dihydro-5-(1-piperidinyl) methyl-3-(-pyridyl)-4H -1,2,4-oxadiazine as an active ingredient.

15. A pharmaceutical product for the treatment and prevention of illnesses resulting from damaged vascular endothelial cells, said product comprising, as an active ingredient, 0.5–95.5 m/m % of a hydroxylamine derivative represented by general formula (I)

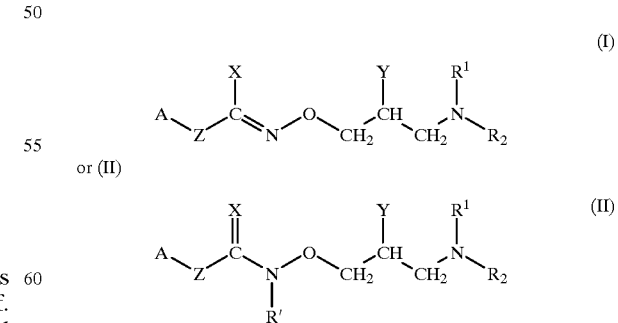

or the salts of optically active forms thereof, wherein $R^1$ and $R^2$ independently comprise a hydrogen atom or a straight or branched alkyl group of 1 to 6 carbon atoms, or $R^1$ and $R^2$ together with the nitrogen atom in-between form a saturated 5–7 membered heterocyclic group, optionally containing additional nitrogen and/or oxygen heteroatoms, A comprises a straight or branched alkyl group of 4 to 12 carbon atoms, a phenyl group, substituted or unsubstituted, containing an alkyl-, haloalkyl- or nitro group as substituent, or a 5–6 membered heteroaromatic ring containing nitrogen, oxygen or sulphur, in general formula (I) Z comprises a covalent bond, and in general formula (II) Z comprises a covalent bond or a =NH group, in general formula (I) X comprises a halogen atom or a —NR$^3$R$^4$ group, wherein R$^3$ and R$^4$ independently comprise a hydrogen atom or a straight or branched alkyl group of 1 to 6 carbon atoms, while in general formula (II) X comprises an oxygen atom, in general formula (II) R' comprises a hydrogen atom or a straight or branched alkyl group of 1 to 6 carbon atoms, and in general formulae (I) and (II) Y comprises a hydrogen atom, a hydroxyl group or an acyloxy group, which contains the acyl part of a long chain fatty acid of 8 to 22 carbon atoms, or of a cyclic aromatic carboxylic acid as its acyl component, and in the compounds of general formula (I) when X comprises a —NR$^3$R$^4$ group and Y comprises a hydroxyl group, the X group is condensed with the Y substituent to form the intramolecular ring represented by general formula (III),

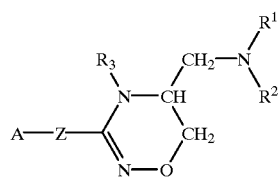

(III)

in which formula A, Z, R$^1$ and R$^2$ comprise the elements defined above or the salts and optically active forms thereof.

* * * * *